(12) United States Patent
Govari et al.

(10) Patent No.: US 10,893,807 B2
(45) Date of Patent: Jan. 19, 2021

(54) MAPPING FORCE AND TEMPERATURE FOR A CATHETER

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US)

(73) Assignee: BIOSENSE WEBSTER (ISRAEL) LTD, Yokneam (IL)

( * ) Notice: Subject to any disclaimer, the term of this patent is extended or adjusted under 35 U.S.C. 154(b) by 316 days.

(21) Appl. No.: 15/966,662

(22) Filed: Apr. 30, 2018

(65) Prior Publication Data

US 2018/0242852 A1    Aug. 30, 2018

Related U.S. Application Data

(62) Division of application No. 14/058,325, filed on Oct. 21, 2013, now Pat. No. 9,980,652.

(51) Int. Cl.
*A61B 5/01* (2006.01)
*A61B 5/00* (2006.01)
(Continued)

(52) U.S. Cl.
CPC ............. *A61B 5/01* (2013.01); *A61B 5/015* (2013.01); *A61B 5/743* (2013.01); *A61B 5/103* (2013.01); *A61B 5/6852* (2013.01); *A61B 18/1492* (2013.01); *A61B 2017/00084* (2013.01); *A61B 2018/00029* (2013.01); *A61B 2018/00357* (2013.01); *A61B 2018/00577* (2013.01); *A61B 2018/00791* (2013.01); *A61B 2018/00815* (2013.01); *A61B 2018/00821* (2013.01); *A61B 2034/2051* (2016.02);
(Continued)

(58) Field of Classification Search
CPC combination set(s) only.
See application file for complete search history.

(56) References Cited

U.S. PATENT DOCUMENTS 5,835,693 A    11/1998 Lynch et al.
7,084,859 B1    8/2006 Pryor
(Continued)

FOREIGN PATENT DOCUMENTS

CN    102106753    6/2011
CN    103327887    9/2013
(Continued)

OTHER PUBLICATIONS

Corresponding CN Office Action dated Jun. 5, 2018.
(Continued)

*Primary Examiner* — Sean P Dougherty
(74) *Attorney, Agent, or Firm* — Louis J. Capezzuto

(57) ABSTRACT

A method for displaying information, including receiving measurements, with respect to an invasive probe inside a body of a subject, of probe parameters consisting of a force exerted by the probe on tissue of the subject and temperatures measured by sensors of the probe. The method further includes, responsively to the measurements, displaying in a single map on a display screen a graphical representation of a distribution of the temperatures in a vicinity of the probe and superimposing thereon a vector representation of the force.

6 Claims, 11 Drawing Sheets

(51) Int. Cl.
  *A61B 17/00*   (2006.01)
  *A61B 18/00*   (2006.01)
  *A61B 18/14*   (2006.01)
  *A61B 90/00*   (2016.01)
  *A61B 34/20*   (2016.01)
  *A61B 5/103*   (2006.01)

(52) U.S. Cl.
  CPC ... *A61B 2090/064* (2016.02); *A61B 2090/065* (2016.02); *A61B 2218/002* (2013.01)

(56) References Cited

U.S. PATENT DOCUMENTS

| | | | |
|---|---|---|---|
| 9,445,725 | B2 | 9/2016 | Govari |
| 9,728,061 | B2 | 8/2017 | Shen et al. |
| 9,980,652 | B2 | 5/2018 | Govari et al. |
| 2003/0153905 | A1 | 8/2003 | Edwards |
| 2003/0199768 | A1* | 10/2003 | Cespedes ........... A61B 5/02007 600/473 |
| 2003/0216621 | A1* | 11/2003 | Alpert ................ A61B 8/12 600/300 |
| 2004/0206365 | A1 | 10/2004 | Knowlton |
| 2006/0253116 | A1 | 11/2006 | Avita |
| 2007/0063691 | A1 | 3/2007 | Yakymyshyn |
| 2007/0293792 | A1* | 12/2007 | Sliwa ................. A61B 5/0051 600/587 |
| 2008/0300487 | A1* | 12/2008 | Govari ............... A61B 8/4254 600/443 |
| 2009/0299142 | A1 | 12/2009 | Uchiyama |
| 2009/0306650 | A1* | 12/2009 | Govari ................ A61B 5/062 606/41 |
| 2010/0298895 | A1* | 11/2010 | Ghaffari ............. A61B 5/01 607/3 |
| 2011/0020779 | A1* | 1/2011 | Hannaford ......... A61B 34/30 434/262 |
| 2011/0130648 | A1 | 6/2011 | Beeckler |
| 2011/0152856 | A1* | 6/2011 | Govari ............... A61B 18/1492 606/34 |
| 2011/0301414 | A1* | 12/2011 | Hotto ................. A61B 1/00055 600/114 |
| 2012/0184863 | A1 | 7/2012 | Harlev et al. |
| 2012/0226130 | A1 | 9/2012 | De Graff |
| 2012/0232388 | A1 | 9/2012 | Curra |
| 2012/0253167 | A1 | 10/2012 | Bonyak |
| 2012/0278005 | A1 | 11/2012 | Sumi |
| 2013/0046175 | A1 | 2/2013 | Sumi |
| 2013/0079650 | A1 | 3/2013 | Turgeman |
| 2015/0035658 | A1 | 2/2015 | Provancher |
| 2016/0143696 | A1* | 5/2016 | Govari ............... A61B 18/1206 606/41 |

FOREIGN PATENT DOCUMENTS

| | | |
|---|---|---|
| EP | 2338428 A1 | 6/2011 |
| EP | 2364664 A1 | 9/2011 |
| EP | 2526887 A1 | 11/2012 |
| JP | H04-127375 | 4/1992 |
| JP | 2014-213431 | 11/2014 |
| WO | 2008/099851 | 8/2008 |
| WO | 08/112005 A1 | 9/2008 |
| WO | 2011/113070 | 9/2011 |
| WO | 2/071388 A2 | 5/2012 |
| WO | 2013052919 | 4/2013 |

OTHER PUBLICATIONS

Tactisys Quartz System by Endosense, Geneva, Switzerland.
European Search Report completed Feb. 24, 2015 for corresponding Application No. EP14189558.
JP Office Action—dated Aug. 27, 2019.
JP H04-127375—English Abstract.

* cited by examiner

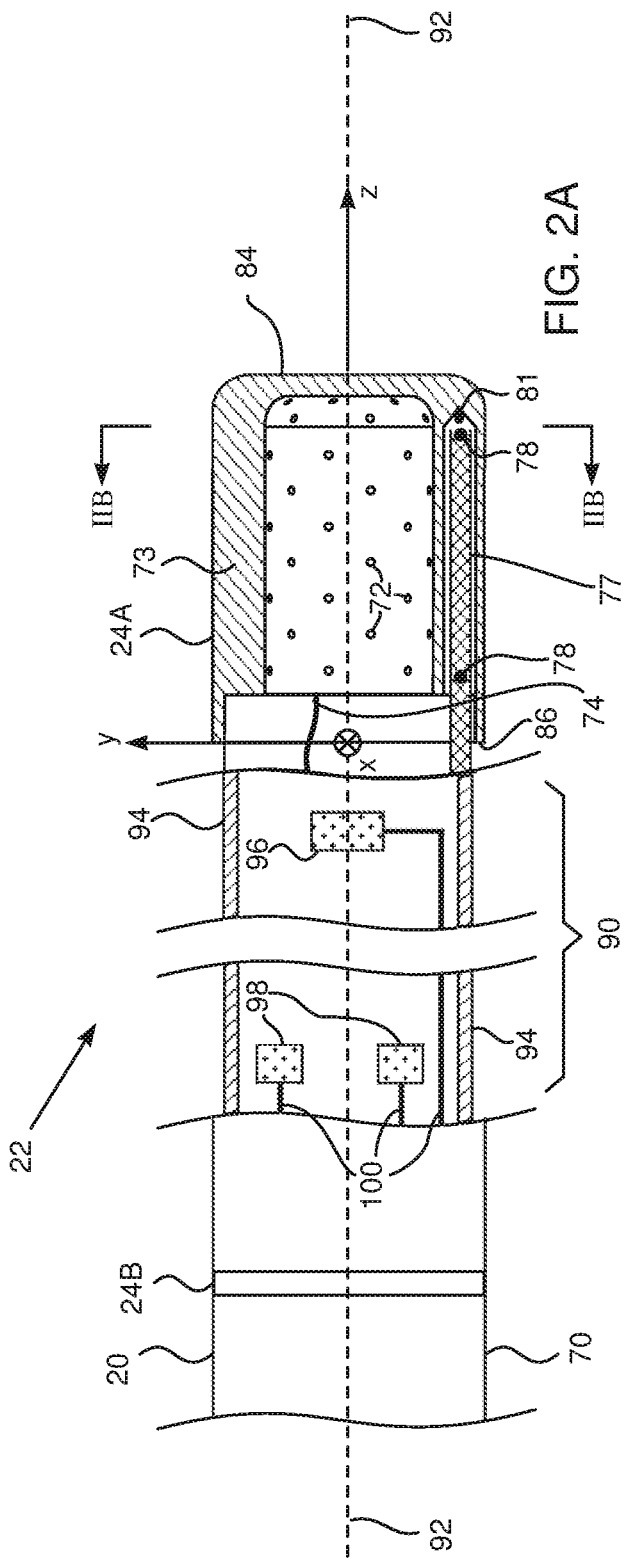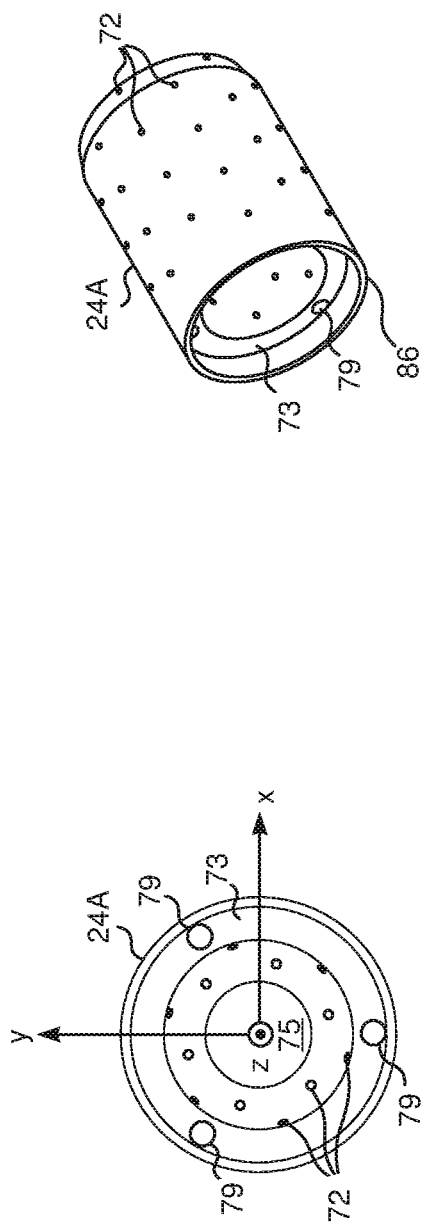

MAPPING FORCE AND TEMPERATURE FOR A CATHETER

This application is a division of U.S. patent application Ser. No. 14/058,325 filed Oct. 21, 2013, the disclosures of all of which are hereby incorporated by reference as if set forth in their entirety herein.

FIELD OF THE INVENTION

The present invention relates generally to graphic displays, and specifically to displays related to the temperature and force measured by a catheter.

BACKGROUND OF THE INVENTION

PCT/US2012/059131 Patent Application to Ghaffari et al., whose disclosure is incorporated herein by reference, describes an apparatus for medical diagnosis. The disclosure provides a series of screen shots of an example graphical user interface demonstrating a variety of conditions simulated with the apparatus.

U.S. Patent Application 2003/0153905 to Edwards, et al. whose disclosure is incorporated herein by reference, describes systems for ablation of hollow organs. The disclosure describes a temperature map in which the temperature data may be used to monitor and control ablation.

U.S. Patent Application 2006/0253116 to Avitall, et al. whose disclosure is incorporated herein by reference, describes catheters, systems, and methods for performing medical procedures such as tissue ablation. The disclosure describes a graphical representation of an internal anatomical structure, which may be displayed in a display window of a monitor.

U.S. Patent Application 2007/0293792 to Sliwa, et. al. whose disclosure is incorporated herein by reference, describes prostate probe systems comprising either a force or pressure sensor mounted on or in a rectally insertable probe or a temperature sensor mounted on or in a rectally insertable probe, or both. The disclosure describes a thermographic or temperature mapping capability.

U.S. Patent Application 2012/0226130 to De Graff, et al. whose disclosure is incorporated herein by reference, describes systems that integrate stretchable or flexible circuitry, including arrays of active devices for enhanced sensing, diagnostic, and therapeutic capabilities. The disclosure describes a graphical presentation and mapping functionality.

U.S. Patent Application 2012/0232388 to Curra, et al. whose disclosure is incorporated herein by reference, describes ultrasound systems and methods for real-time noninvasive spatial temperature estimation. The disclosure claims that strain and spectral information can be compounded and correlated with both strain-based and spectral-based temperature calibration maps.

U.S. Patent Application 2013/0079650 to Turgeman, et al. whose disclosure is incorporated herein by reference, describes a graphic user interface for physical parameter mapping. The disclosure describes receiving a selection from a user of a value in a parameter sub-range and displaying a candidate location for further measurement.

Endosense, of Geneva, Switzerland, produce a "Tactisys Quartz" system. The system is claimed to allow visualization of contact force between a catheter tip of the system and a heart wall.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method for displaying information, including:

receiving measurements, with respect to an invasive probe inside a body of a subject, of probe parameters consisting of a force exerted by the probe on tissue of the subject and temperatures measured by sensors of the probe; and responsively to the measurements, displaying in a single map on a display screen a graphical representation of a distribution of the temperatures in a vicinity of the probe and superimposing thereon a vector representation of the force.

Typically, the vector representation includes a first indication of a magnitude of the force and a second indication of a force-direction of the force.

In a disclosed embodiment the vector representation includes an arrow, the first indication includes a width of the arrow, and the second indication includes a combination of a length of the arrow and a direction of the arrow.

In a further disclosed embodiment the vector representation includes an arrow and a text box associated with the arrow, the first indication includes text within the text box, and the second indication includes a combination of a length of the arrow and a direction of the arrow.

In a yet further disclosed embodiment the vector representation includes a first circle having a first center, the graphical representation of the distribution includes a second circle having a second center, the first indication includes a diameter of the first circle, and the second indication consists of a combination of a distance between the first and second centers and a direction therebetween.

In an alternative embodiment the method includes calculating a center of the graphical representation, and displaying the center in the single map.

There is further provided, according to an embodiment of the present invention embodiment of the present invention, apparatus for displaying information, including:

a probe, configured to be inserted into a body of a subject;

a force sensor attached to the probe, coupled to provide a force signal indicative of a force exerted by the probe on tissue of the subject;

temperature sensors attached to the probe, coupled to provide temperature signals of temperatures in a vicinity of the probe;

a display screen; and a processor coupled to receive the force signal and the temperature signals, to display in a single map on the display screen a graphical representation of a distribution of the temperatures, and to superimpose thereon a vector representation of the force.

The present disclosure will be more fully understood from the following detailed description of the embodiments thereof, taken together with the drawings, in which:

BRIEF DESCRIPTION OF THE DRAWINGS

FIGS. 2A, 2B, and 2C schematically illustrate a distal end of a probe used in the procedure of FIG. 1, according to an embodiment of the present invention;

DETAILED DESCRIPTION OF EMBODIMENTS

Figure 1:
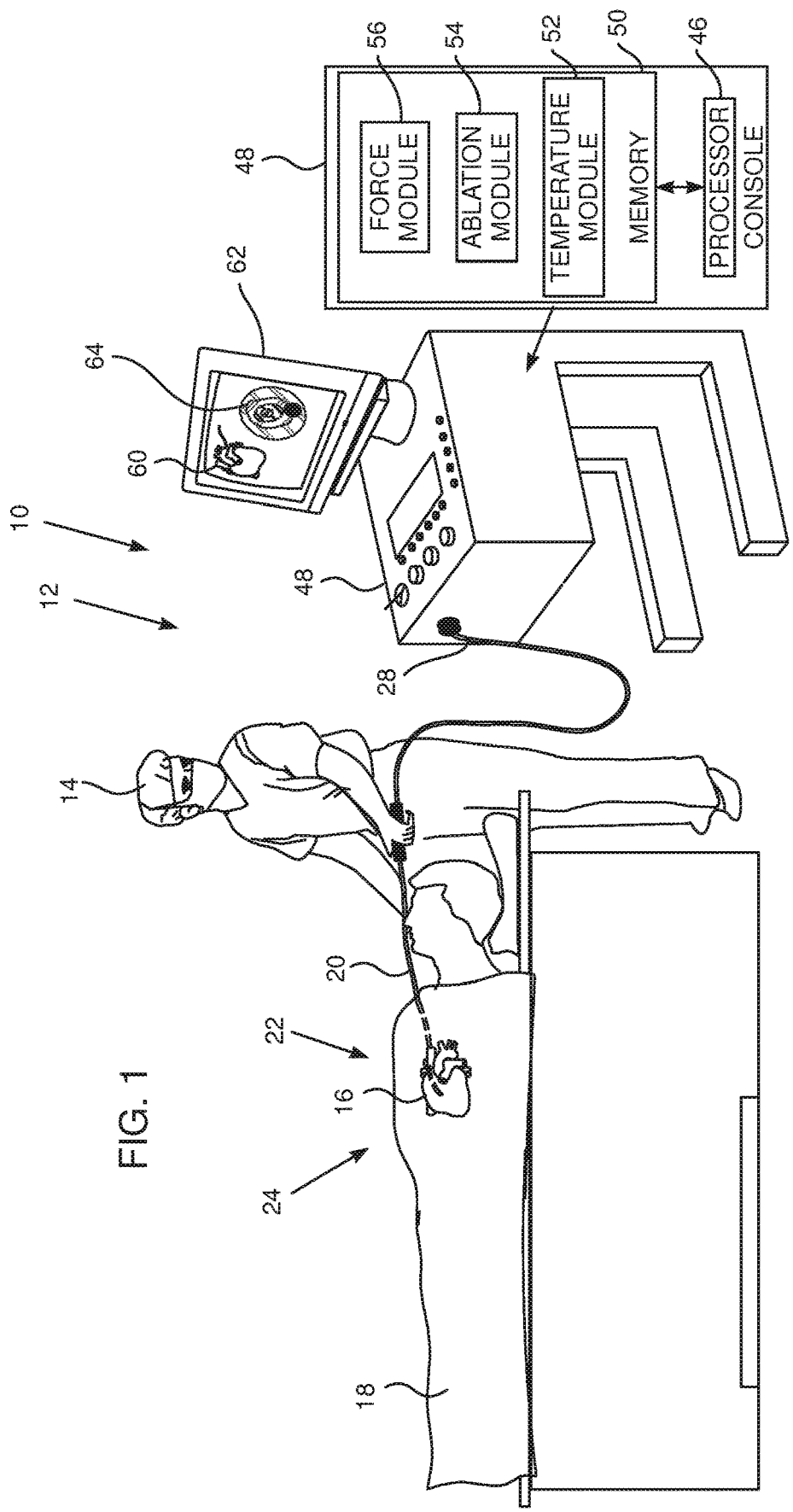
FIG. 1 is a schematic illustration of an invasive medical procedure, according to an embodiment of the present invention.

In the following description, like elements in the drawings are identified by like numerals, and the like elements are differentiated as necessary by appending a letter to the identifying numeral.

FIG. 1 is a schematic illustration of an invasive medical procedure 10 using apparatus 12, according to an embodiment of the present invention. The procedure is performed by a medical professional 14, and, by way of example, procedure 10 is assumed to comprise ablation of a portion of a myocardium 16 of the heart of a human patient 18. In order to perform the ablation, professional 14 inserts a probe 20 into a lumen of the patient, so that a distal end 22 of the probe enters the heart of the patient. Distal end 22 comprises electrodes 24 mounted on the outside of the distal end, the electrodes contacting respective regions of the myocardium. Probe 20 has a proximal end 28. Distal end 22 of the probe is described in more detail below with reference to FIGS. 2A and 2B.

Apparatus 12 is controlled by a system processor 46, which is located in an operating console 48 of the apparatus. During the procedure, processor 46 typically tracks a location and an orientation of distal end 22 of the probe, using any method known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62.

In order to operate apparatus 12, processor 46 communicates with a memory 50, which has a number of modules used by the processor to operate the apparatus. Thus, memory 50 comprises a temperature module 52, an ablation module 54, and a force module 56, the functions of which are described below. Memory 50 typically comprises other modules, such as a tracking module for operating the tracking method used by processor 46, and an irrigation module allowing the processor to control irrigation provided for distal end 22. For simplicity, such other modules, which may comprise hardware as well as software elements, are not illustrated in FIG. 1.

Processor 46 uses results of measurements of temperature and force, acquired by modules 52 and 56, to display on screen 62 a combined force-temperature map 64. Embodiments of force-temperature map 64 are described in more detail below.

FIGS. 2A, 2B, and 2C schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, and FIG. 2C is a perspective view of a section of the distal end. An insertion tube 70 extends along the length of the probe and is connected at the termination of its distal end to a conductive cap electrode 24A, which is assumed herein to be used for ablation. FIG. 2C is a schematic perspective view cap electrode 24A. Cap electrode 24A has an approximately plane conducting surface 84 at its distal end and a substantially circular edge 86 at its proximal end. Conductive cap electrode 24A is herein also termed. The ablation electrode. Proximal to ablation electrode 24A there are typically other electrodes such as electrode 24B. Typically, insertion tube 70 comprises a flexible, biocompatible polymer, while electrodes 24A, 21B comprise a biocompatible metal, such as gold or platinum, for example. Ablation electrode 24A is typically perforated by an array of irrigation apertures 72.

An electrical conductor 74 conveys radio-frequency (PD) electrical energy from ablation module 54 (FIG. 1), through insertion tube 70, to electrode 24A, and thus energizes the electrode to ablate myocardial tissue with which the electrode is in contact. Module 54 controls the level of RF power dissipated via electrode 34A. During the ablation procedure, cooling fluid flowing out through apertures 72 may irrigate the tissue under treatment.

Temperature sensors 78 are mounted within conductive cap electrode 24A at locations that are arrayed around the distal tip of the probe, both axially and circumferentially. In this example, cap 24A contains six sensors, with one group in a distal location, close to the tip, and the other group in a slightly more proximal location. This distribution is shown only by way of example, however, and greater or smaller numbers of sensors may be mounted in any suitable locations within the cap. Sensors 78 may comprise thermocouples, thermistors, or any other suitable type of miniature temperature sensor. These sensors are connected by leads 80 running through the length of insertion tube 70 to provide temperature signals to temperature module 52.

In a disclosed embodiment cap 24A comprises a side wall 73 that is relatively thick, on the order of 0.5 mm thick, in order to provide the desired thermal insulation between temperature sensors 78 and the cooling fluid inside a central cavity 75 of the tip. The cooling fluid exits cavity 75 through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable glue 81, such as epoxy. U.S. patent application Ser. No. 13/716,578, which is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention. Another arrangement of sensors is described in U.S. patent application Ser. No. 13/716,578, referenced above.

In addition to the temperature sensors, distal end 22 comprises a force sensor 90, which is configured to measure the force exerted by the distal end on tissue contacted by the distal end. Force sensor 90 generates signals in response to the measured force, and the signals are transferred to force module 56, which operates the sensor and which calculates a value for the magnitude, as well as a value for the direction, of the force exerted. The direction of the force exerted is measured with respect to an axis 92, typically the axis of symmetry, of distal end 22.

In the description herein, distal end 22 is assumed to define a set of xyz orthogonal axes, where axis 92 corresponds to the z axis of the set, and orthogonal x and y axes are in any convenient xy plane orthogonal to the z axis. For simplicity, the xy plane is herein assumed to correspond to the plane defined by circle 86, the origin of the xyz axes is assumed to be the center of the circle.

Force sensor 90 may comprise any convenient sensor of force or pressure known in the art. By way of example, herein force sensor 90 is assumed to operate by measuring the deflection, parallel to z axis 92 and orthogonal to the axis, i.e., in an xy plane, of a cylindrically shaped spring 94. The deflection of spring 94 may be measured by transmitting an alternating magnetic field from a magnetic transmitter 96 located in proximity to the distal end of the spring, and measuring the received magnetic field in magnetic receivers 98 located at the proximal end of the spring. Typically transmitter 96 and receivers 98 are coils, transmitter 96 being located on axis 92, and receivers 98 being distributed symmetrically around the axis. In force sensor 90 there are three receivers 98 (two are shown in the figure). Operating signals between force module 90 and the transmitter and the receivers are transferred by conductors 100, and enable the force module to generate a unique value for the magnitude of a given force, as well as a unique value for the direction of the force with respect to the xyz axes of distal end 22. Force sensors similar to force sensor 90 are described in U.S. Patent Applications 2009/0306650 to Govari et al., 2011/0130648 to Beeckler et al., and 2012/0253167 to Bonyak et al., all of which are incorporated herein by reference.

Typically, distal end 22 contains other functional components, which are outside the scope of the present disclosure and are therefore omitted for the sake of simplicity. For example, the distal end of the probe may contain steering wires, as well as sensors of other types, such as a position sensor. Probes containing components of these kinds are described, for example, in U.S. Patent Applications 2009/0306650 and 2011/0130648, referenced above.

Figure 3B:
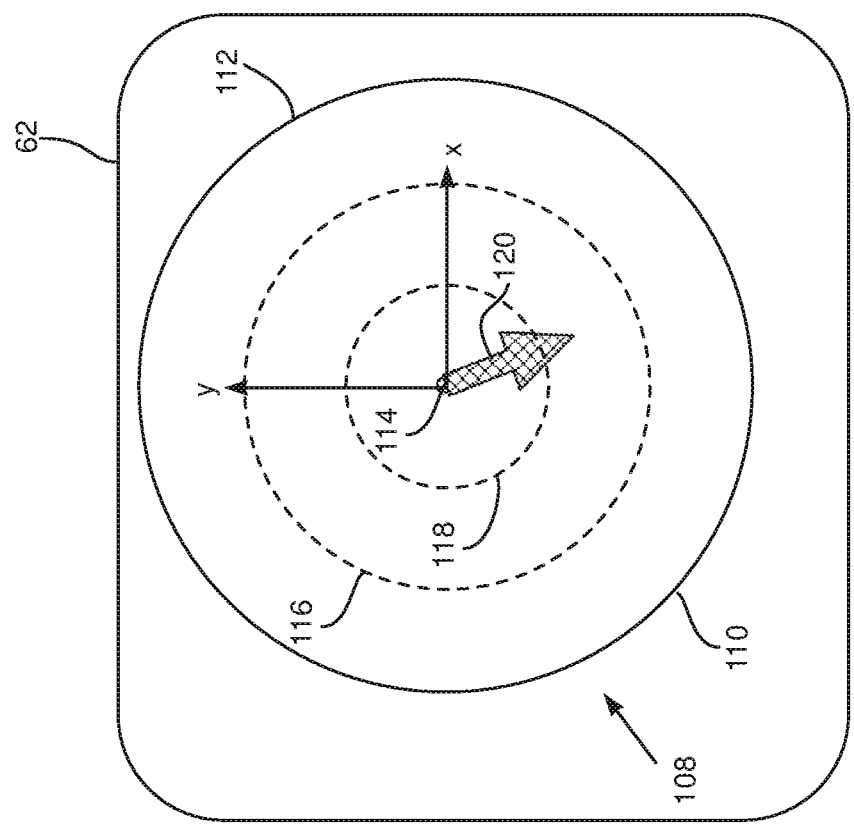
FIG. 3B is a schematic diagram illustrating a vector representation of the force exerted by the distal end, as displayed on the screen, according to an embodiment of the present invention.
Figure 3A:
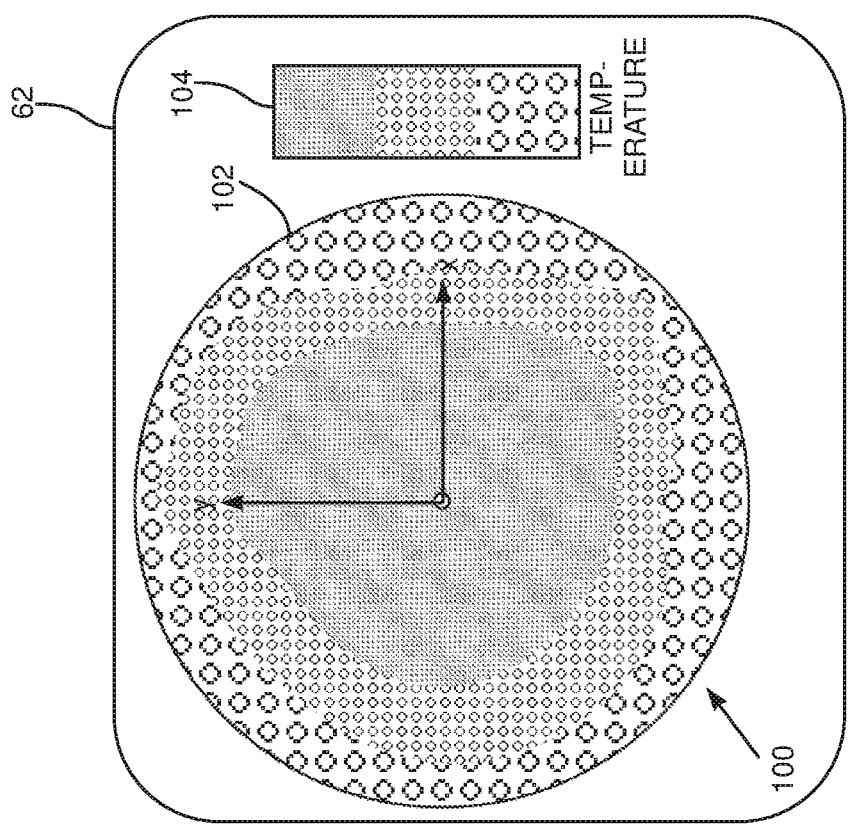
FIG. 3A is a schematic diagram illustrating a temperature distribution in the vicinity of a distal end of the probe, as displayed on a screen, according to an embodiment of the present invention.

FIG. 3A is a schematic diagram illustrating a temperature distribution in the vicinity of distal end 22, as displayed on screen 62, according to an embodiment of the present invention. Using measurements provided by temperature sensors 78, as well as knowledge of the positions of the sensors with respect to each other and with respect to the xyz axes of distal end 22, processor 46 uses temperature module 52 to generate a two-dimensional (2D) temperature map 100. 2D map 100 is a graphical representation of the three-dimensional (3D) distribution of the temperatures of the external surface of electrode 24A, and is assumed to be drawn as a 2D projection with respect to the xyz axes defined above for distal end 22. Map 100 is drawn as a circular map, a bounding circle 102 of the map corresponding with edge 86 of electrode 24A. The generation of 2D map 100 from measurements of sensors 78 typically uses interpolation and extrapolation from the measurements, as is known in the art.

As stated above, 2D map 100 is a 2D projection of a 3D distribution of temperatures. One type of projection that may be used, based on angles subtended by a line through the origin of the xyz axes to the z-axis (FIG. 2A), is described in more detail with respect to FIG. 3B, which illustrates a projection used to represent the direction of a force vector. As is assumed in the following description, the same type of projection may be used to represent the temperature distribution and the force vector. However, there is no necessity that the projections are the same, and in some embodiments the projections are different.

2D map 100 is typically a color map showing the different temperatures of the external surface of electrode 24A, and a legend 104 may be displayed with the map showing values of the temperatures for the different colors. (In the figures different colors are schematically illustrated by different shadings.) In some embodiments the numerical values measured by each of sensors 78 may also be displayed on map 100. For simplicity, the display of such numerical values is not illustrated in FIG. 3A.

FIG. 3B is a schematic diagram illustrating a vector representation 108 of the force exerted by distal end 22, as displayed on screen 62, according to an embodiment of the present invention. As explained above force sensor 90 is able to generate signals which may be used by force module 56 and processor 46 to find a magnitude of the force exerted by distal end 22, as well as a direction of the force. The direction of the force may be measured relative to the xyz axes of distal end 22. Starting with a 3D vector representation of the force, the 3D direction may be represented on a 2D surface such as that of screen 62 by any convenient projection of a 3D direction. By way of example, a projection used herein is similar to a polar stereographic projection, generating a circular map 110. Map 110 has a bounding circle 112, which represents directions orthogonal to the z-axis referred to above. A center 114 of map 110 represents directions along the z-axis. In the exemplary projection illustrated herein, a broken circle 116 corresponds to a direction at 60° to the z-axis, and a broken circle 118 corresponds to a direction at 30° to the z-axis. Circles representing angles to the z-axis, such as circles 116 and 118, are also herein termed angular circles. By way of example, in the projection assumed herein a diameter of an angular circle is in direct proportion to the angle it represents, so that circles 112, 116, and 118 have diameters in the ratio of 3:2:1.

Representation 108 comprises a variable length arrow 120 representing the direction of the force exerted by distal end 22, which has been drawn on map 110. Arrow 120 has a start point corresponding with the center of circle 112, and an end point corresponding to the angle subtended by the distal end force to the z-axis, so that a length of the arrow is a function of the angle of the force measured with respect to the z-axis. Thus in FIG. 3B, the distal end force is in a direction that is approximately 40° to the z-axis. In representation 108 arrow 120 has a direction with respect to the xy axes corresponding to a projection of a 3D representation of the force vector on the xy plane. FIG. 3B illustrates arrow 120 as subtending an angle of approximately −70° with respect to the x-axis.

In order to represent the magnitude of the force in representation 108, in a disclosed embodiment a width of arrow 120 is varied according to the magnitude. By varying the width of the arrow, representation 108 is a complete vector representation of the magnitude and the direction of the force exerted by distal end 22.

Figure 3D:
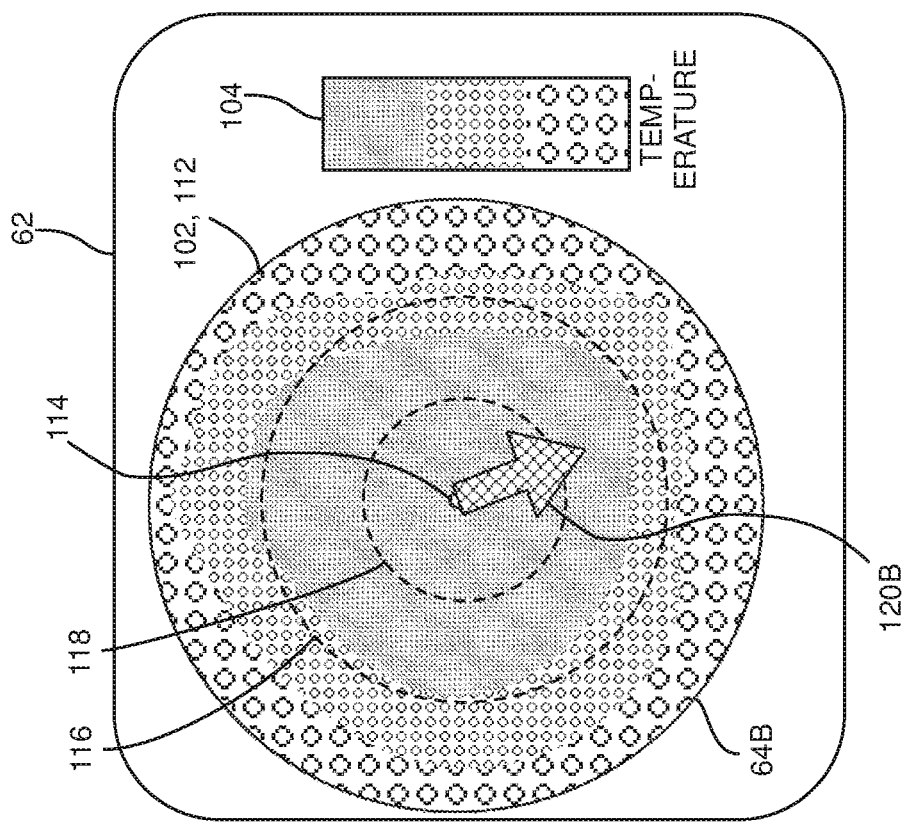
FIG. 3C and FIG. 3D are respective illustrations of a first single combined force-temperature map and a second single combined force-temperature map, according to embodiments of the present invention.
Figure 3C:
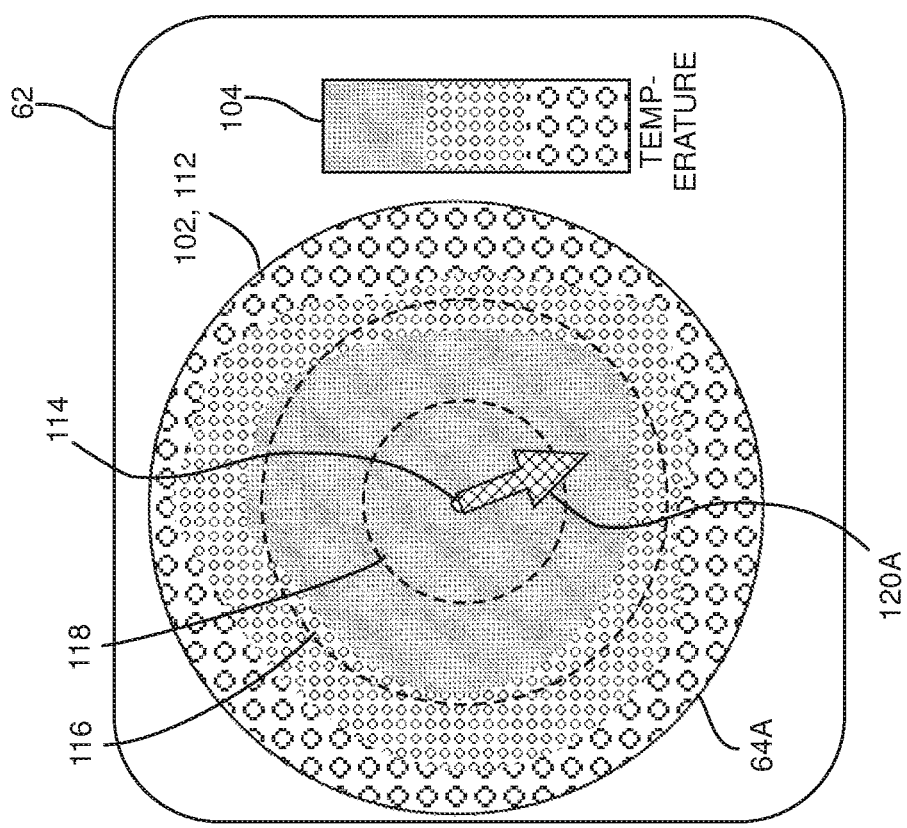

FIG. 3C and FIG. 3D are respective illustrations of a single combined force-temperature map 64A and a single combined force-temperature map 64B, according to embodiments of the present invention. In the following description, elements indicated by the same reference numerals in FIGS. 3A, 3B, 3C, and 3D are generally similar in function. Maps 64A and 64B are formed by having circles 102 and 112 (FIGS. 3A and 3B) the same diameter, and superimposing the resulting circular temperature map 100 and force representation 108 on each other, so as to form single maps 64A and 64B on screen 62. Thus combined force-temperature map 64A displays both the temperature distribution in the vicinity of distal end 22 and the force exerted by the distal end. For a different case, combined force-temperature map 64B also displays the temperature distribution and the force. In both maps the force is displayed as an arrow, and a color of the arrow is selected so that the arrow is easily differentiated from the temperature distribution.

In the presentation of single map 64 on screen 62, an operator of the system may choose to display all, some, or none of the xyz axes and the angular circles. By way of example, in the examples illustrated herein, angular circles, but not the xyz axes, are displayed.

Single maps 64A and 64B have the same temperature distribution, and the force is in the same direction. (approximately 40° to the z-axis and −70° to the x-axis). However, the magnitudes of the force in the two maps is different, the difference being presented on screen 62 as different widths of an arrow 120A in map 64A and an arrow 120B in map 64B. Usually a width of the arrow representing the force as configured to be proportional to, and typically directly proportional to, a magnitude of the force. FIGS. 3C and 3D show that arrow 120B (map 64B) is wider than arrow 120A (map 64A). Thus, for example, the force in map 64A may be 2 g, and the force in map 64B may be 3 g.

Figure 4A:
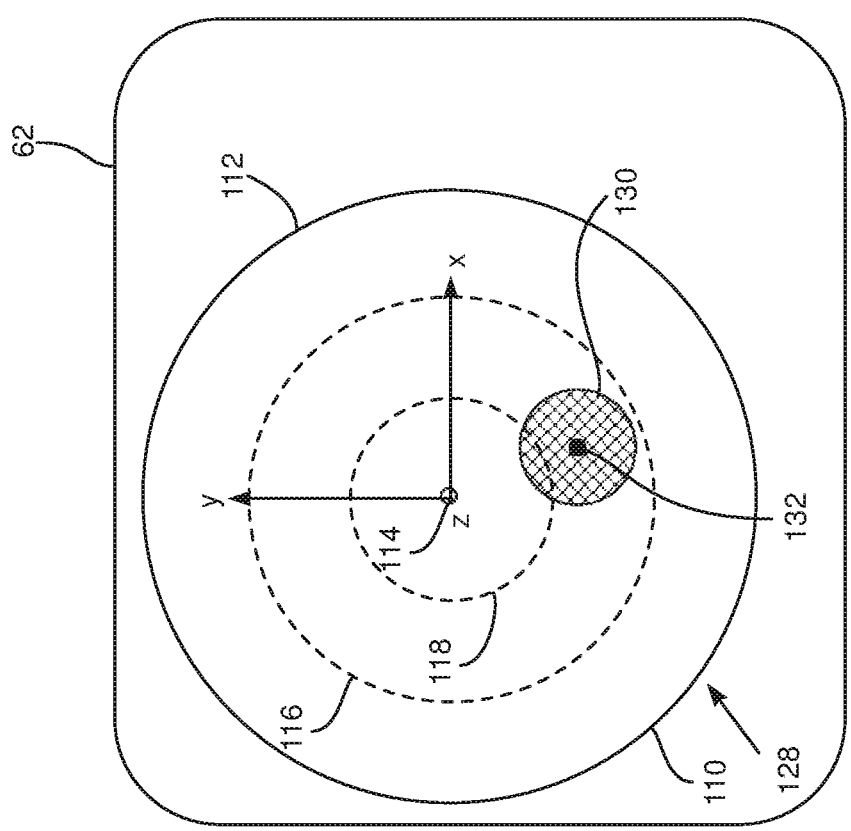
FIG. 4A is a schematic diagram illustrating a vector representation of the force exerted by distal the end 22, as displayed on the screen, according to an alternative embodiment of the present invention.

FIG. 4A is a schematic diagram illustrating a vector representation 128 of the force exerted by distal end 22, as displayed on screen 62, according to an alternative embodiment of the present invention. Apart from the differences described below, vector representation 128 (FIG. 4A) is generally similar to representation 108 (FIG. 3B), and elements indicated by the same reference numerals in both representations are generally similar in function and in properties.

Rather than using an arrow to represent the force exerted by distal end 22, representation. 128 uses a circle 130. A center 132 of the circle, measured with respect to center 114 and the xy axes, represents the direction of the force exerted by the distal end. FIG. 4A has been drawn assuming the force on distal end 22 is the same as that illustrated in FIG. 3B. Thus in FIG. 4A, angular circles 116 and 118 indicate that center 132 in a direction that is approximately 40° to the z-axis, and an imaginary line between centers 114 and 132 subtends an angle of approximately −70° with respect to the x-axis.

In order to represent the magnitude of the force in representation 128, in a disclosed embodiment a diameter of circle 130 is varied according to the magnitude. By varying the diameter of the circle, representation 128 is a complete vector representation of the magnitude and the direction of the force exerted by distal end 22.

Figure 4C:
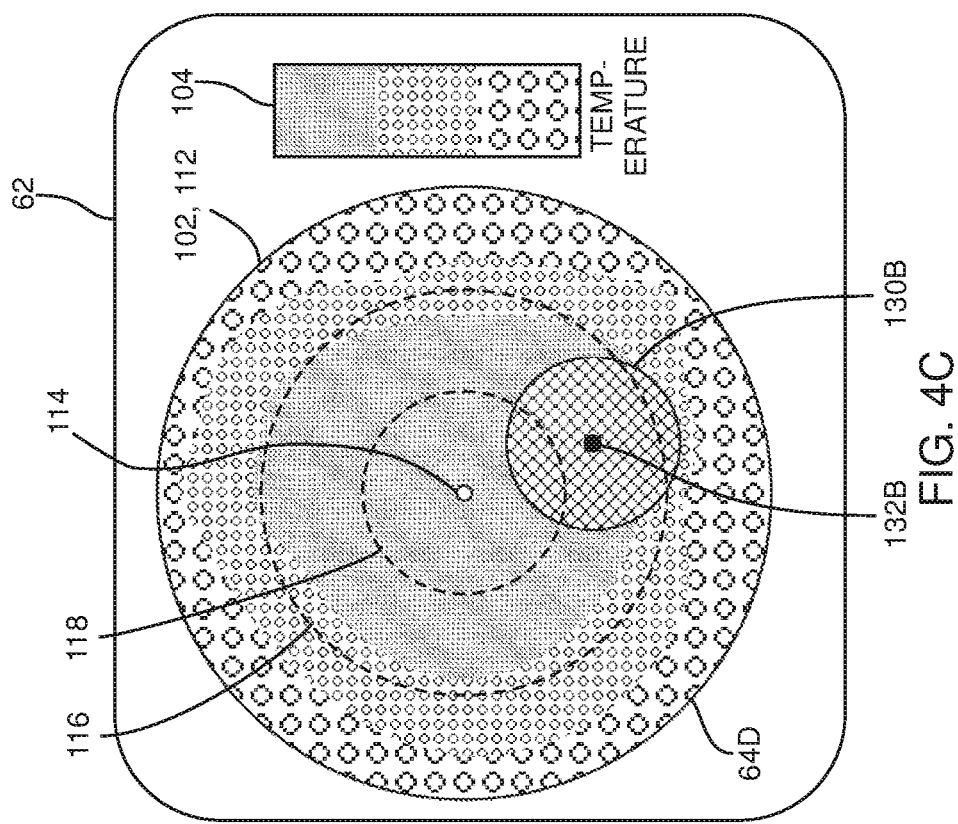
FIG. 4B and FIG. 4C are respective illustrations of single combined force-temperature maps, according to alternative embodiments of the present invention.
Figure 4B:
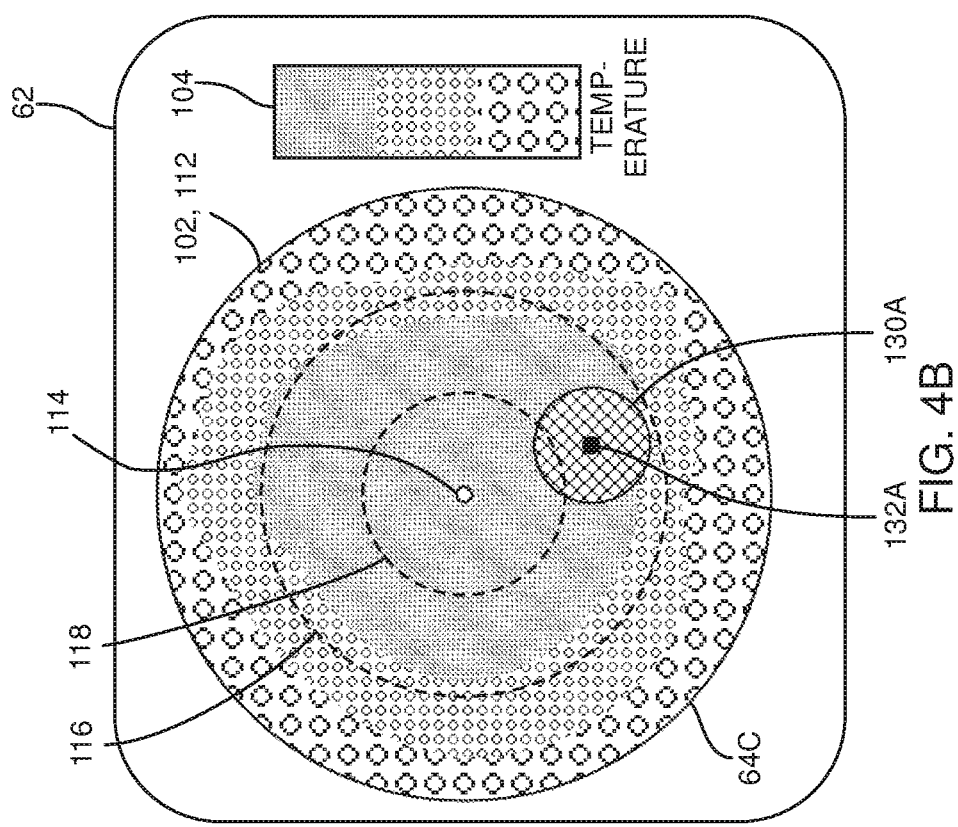

FIG. 4B and FIG. 4C are respective illustrations of a single combined force-temperature map 64C and a single combined force-temperature map 64D, according to alternative embodiments of the present invention. In contrast to maps 64A and 64B, maps 64C and 64D are formed by superimposing temperature map 100 (FIG. 3A) and force representation 128 (FIG. 4A) on each other, and displaying the resulting combined force-temperature map on screen 62. Thus combined force-temperature map 64C displays both the temperature distribution in the vicinity of distal end 22 and the force exerted by the distal end. For a different case, combined force-temperature map 64D also displays the temperature distribution and the force. In both maps the force is displayed as a circle, and a color of the circle is selected so that the circle is easily differentiated from the temperature distribution.

Single maps 64C and 64D have the same temperature distribution, and the force is in the same direction (approximately 40° to the z-axis and −70° to the x-axis), as is indicated by the same positions of centers 132A and 132B in their respective circles. However, the magnitudes of the force in the two maps is different, the difference being presented on screen 62 as different diameters of a circle 130A in map 64C and a circle 130B in map 64D. Usually a diameter of the circle representing the force is configured to be proportional to, and typically directly proportional to, a magnitude of the force. FIGS. 4B and 4C show that circle 130B (map 64D) has a larger diameter than circle 130A (map 64C). Thus, for example, the force in map 64C may be 2 g, and the force in map 64D may be 3 g.

Figure 5A:
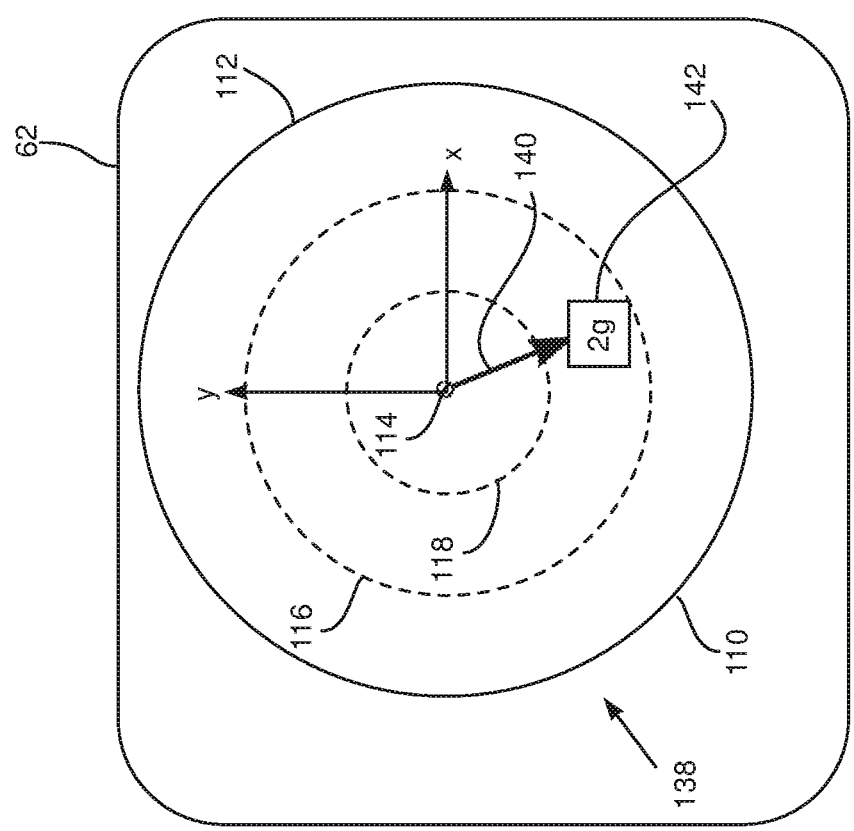
FIG. 5A is a schematic diagram illustrating a vector representation of the force exerted by the distal end, according to a further alternative embodiment of the present invention.

FIG. 5A is a schematic diagram illustrating a vector representation 138 of the force exerted by distal end 22, as displayed on screen 62, according to a further alternative embodiment of the present invention. Apart from the differences described below, vector representation 138 (FIG. 5A) is generally similar to representation 108 (FIG. 3B), and elements indicated by the same reference numerals in the two representations are generally similar in function and in properties.

Rather than using a variable length arrow having a variable width (as described above for representation 108) to represent the force exerted by distal end 22, representation 138 uses a variable length arrow 140 with a constant width. Except that it is invariant with regard to width, arrow 140 is generally similar to arrow 120 (FIG. 3B), so that a length of arrow 140 is a function of the angle subtended by the force with the z-axis. FIG. 5A has been drawn assuming the force on distal end 22 is the same as that illustrated in FIG. 3B. Thus, in FIG. 5A, the end or length of arrow 140 indicates that the force is in a direction that is approximately 40° to the z-axis, and the direction of the arrow indicates that the force subtends an angle of approximately −70° with respect to the x-axis.

In order to represent the magnitude of the force in representation 138, in a disclosed embodiment a text box 142 is "attached" to arrow 140 and a value corresponding to the force magnitude is entered into the text box. By way of example, text box 142 is attached to the head of arrow 140, but in other embodiments text box 142 may be in any convenient position with respect to the arrow. Text within the text box gives a magnitude of the force, so that representation 138 is a complete vector representation of the force on distal end 22.

Figure 5C:
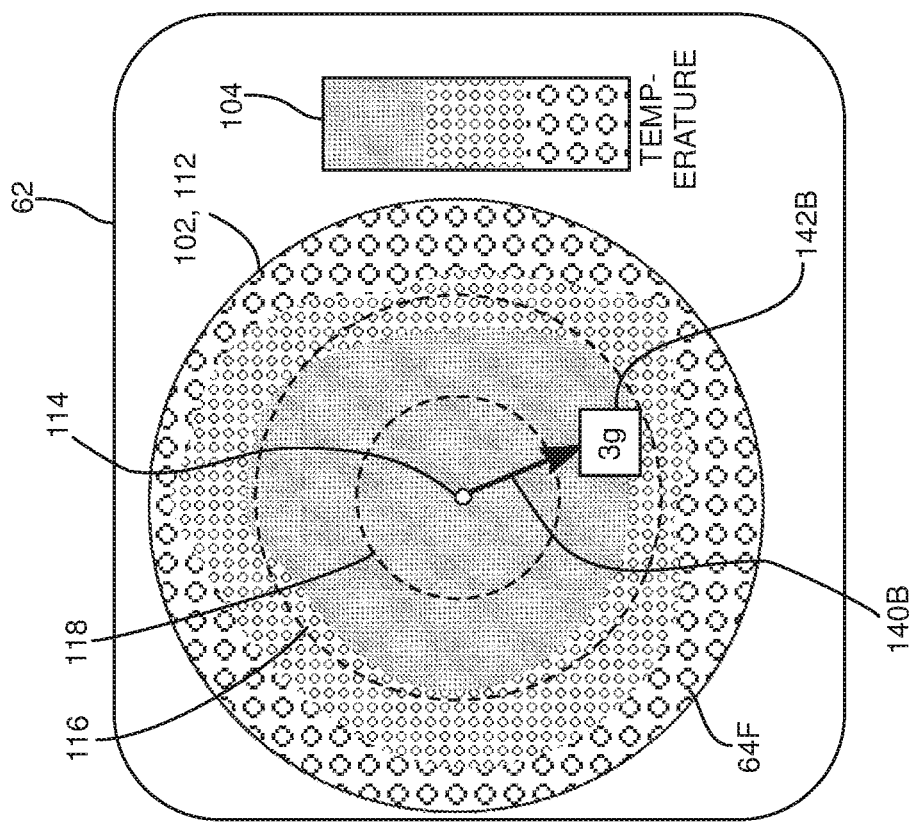
FIG. 5B and FIG. 5C are respective illustrations of single combined force-temperature maps, according to further alternative embodiments of the present invention.
Figure 5B:
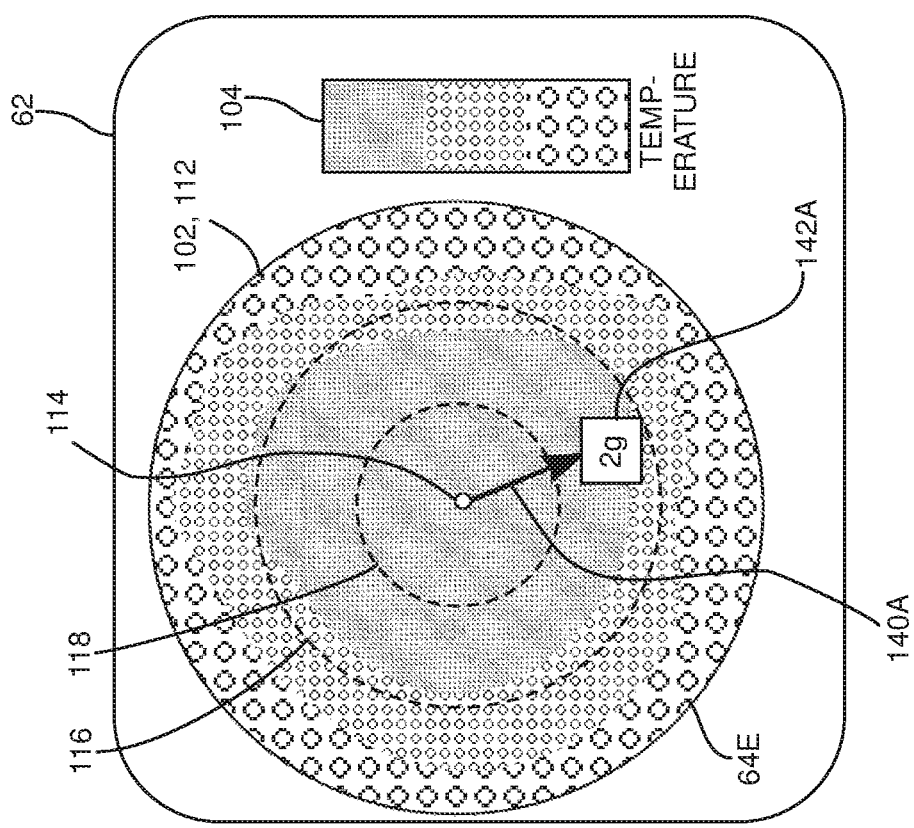

FIG. 5B and FIG. 5C are respective illustrations of a single combined force-temperature map 64E and a single combined force-temperature map 64F, according to further alternative embodiments of the present invention. Except for the following differences, maps 64E and 64F are generally similar to maps 64A and 64B. However, in contrast to maps 64A and 64B, maps 64E and 64F are formed by superimposing temperature map 100 (FIG. 3A) and force representation 138 (FIG. 5A) on each other, and displaying the resulting combined force-temperature map on screen 62. Thus combined force-temperature map 64E displays both the temperature distribution in the vicinity of distal end 22 and the force exerted by the distal end. For a different case, combined force-temperature map 64F also displays the temperature distribution and the force. In both maps the direction of the force is displayed as an arrow.

Single maps 64E and 64F have the same temperature distribution, and the force is in the same direction (approximately 40° to the z-axis and −70° to the x-axis), as is indicated by the same directions and lengths of arrows 140A and 140B. However, the magnitudes of the force in the two maps are different, the difference being presented on screen 62 as a text box 142A in map 64E and as a text box 142B in map 64F. Thus, for example, the force in map 64E is 2 g, and the force in map 64F is 3 g.

Figure 6B:
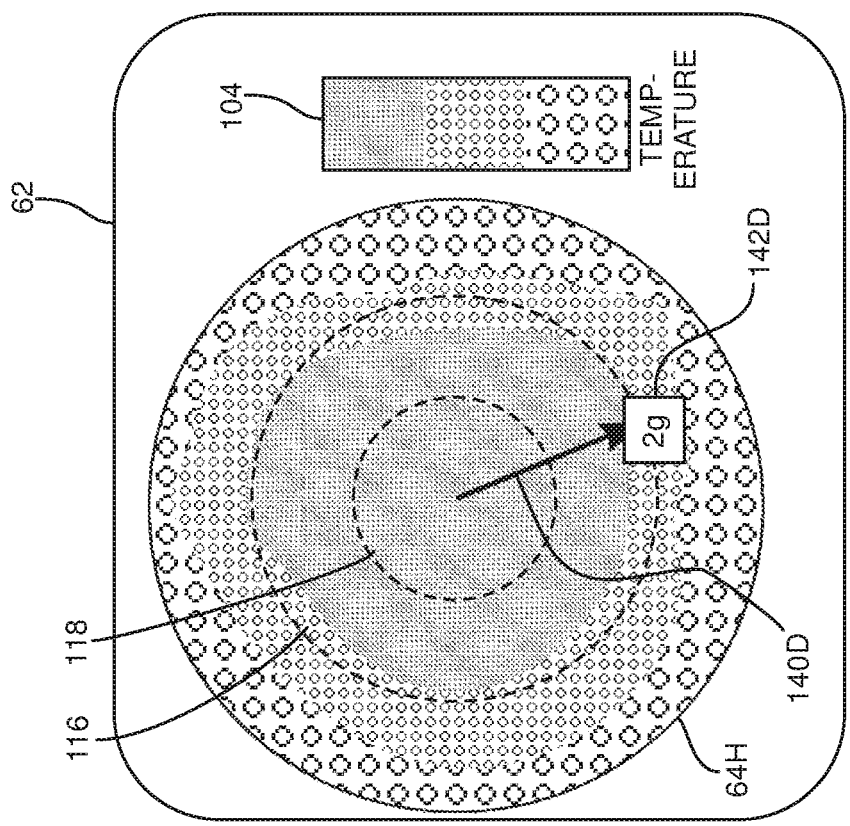
FIG. 6A and FIG. 6B are respective illustrations of single combined force-temperature maps, according to disclosed embodiments of the present invention.
Figure 6A:
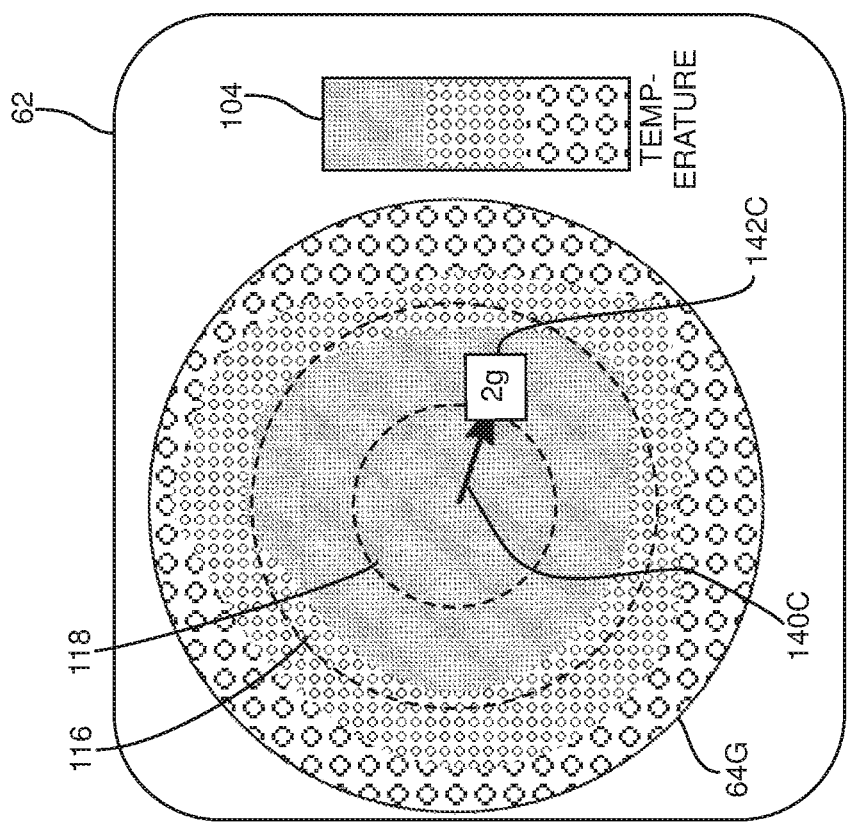

FIG. 6A and FIG. 6B are respective illustrations of a single combined force-temperature map 64G and a single combined force-temperature map 64H, according to embodiments of the present invention. Except for the following differences, maps 64G and 64H are generally similar to maps 64E and 64F. Maps 64E, 64F, 64G, and 64H are all combined force-temperature maps, using the embodiment illustrated in FIGS. 5A-5C, with the same temperature distribution. However, while maps 64E, 64F illustrate the force as having the same direction and a different magnitude, maps 64G, 64H illustrate the force as having the same magnitude of 2 g, but different force directions. Thus map 64G illustrates the force as subtending approximately 30° to the z-axis, and −20° to the x-axis, and map 64H illustrates the force as subtending approximately 60° to the z-axis, and −70° to the x-axis.

Figure 7B:
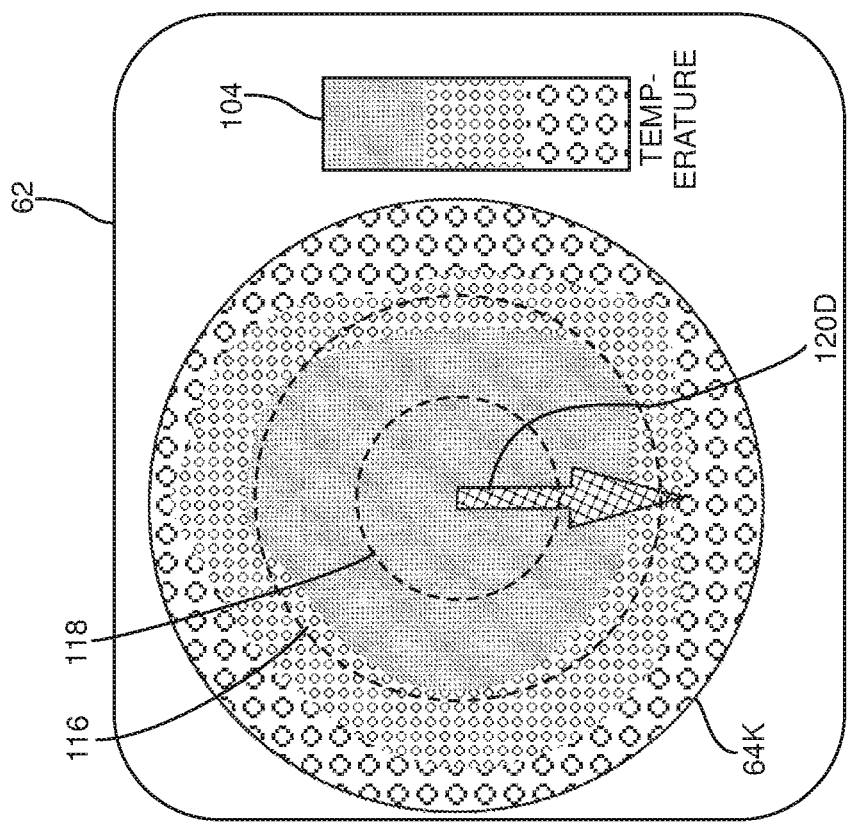
FIG. 7A and FIG. 7B are respective illustrations of single combined force-temperature maps, according to further disclosed embodiments of the present invention.
Figure 7A:
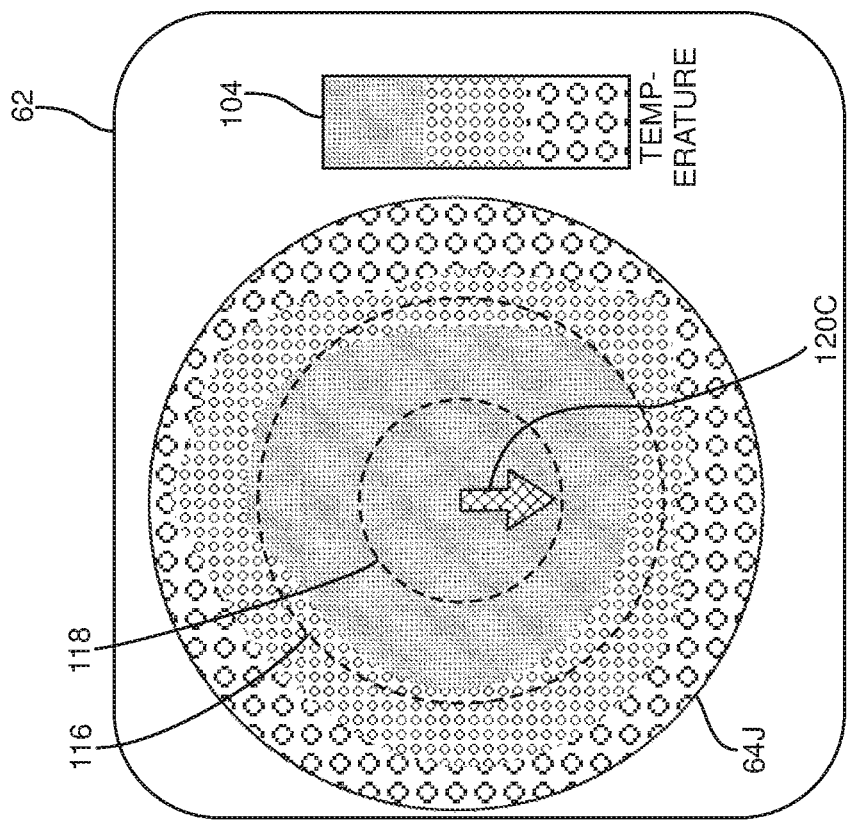

FIG. 7A and FIG. 7B are respective illustrations of a single combined force-temperature map 64J and a single combined force-temperature map 64K, according to embodiments of the present invention. Except for the following differences, maps 64J and 64K are generally similar to maps 64A and 64B. Maps 64A, 64B, 64J, and 64K are all combined force-temperature maps, using the embodiment illustrated in FIGS. 3B-3D, with the same temperature distribution. However, while maps 64A, 64B illustrate the force as having the same direction and a different magnitude, shown by the different arrow widths, maps 64J, 64K illustrate the force as having the same magnitude, since arrows 120C and 120D have the same widths. However, the forces in the two maps have different directions. Thus map 64J illustrates the force as subtending approximately 30° to the z-axis, and −90° to the x-axis, and map 64K illustrates the force as subtending approximately 70° to the z-axis, and −90° to the x-axis.

By presenting the force (in magnitude and direction) together with the temperature distribution in a single map, embodiments of the present invention facilitate the ablation process performed by a physician, by enabling the physician to see the relative alignment between the force and the temperature distribution. For example, during the ablation process, the physician may desire that the force is directed to the hottest part of the temperature distribution, so that the force "aligns" with the temperature. This is typically the desired state during ablation of a single region. Alternatively, the physician may desire that the force is directed in a particular direction away from the hottest part of the temperature distribution. This is typically the desired state during ablation along a line. Embodiments of the present invention facilitate these types of alignment by allowing the physician to mark a "center" of the temperature, which enables the physician to compare the direction of the force, and the "direction" of the temperature distribution.

Figure 8B:
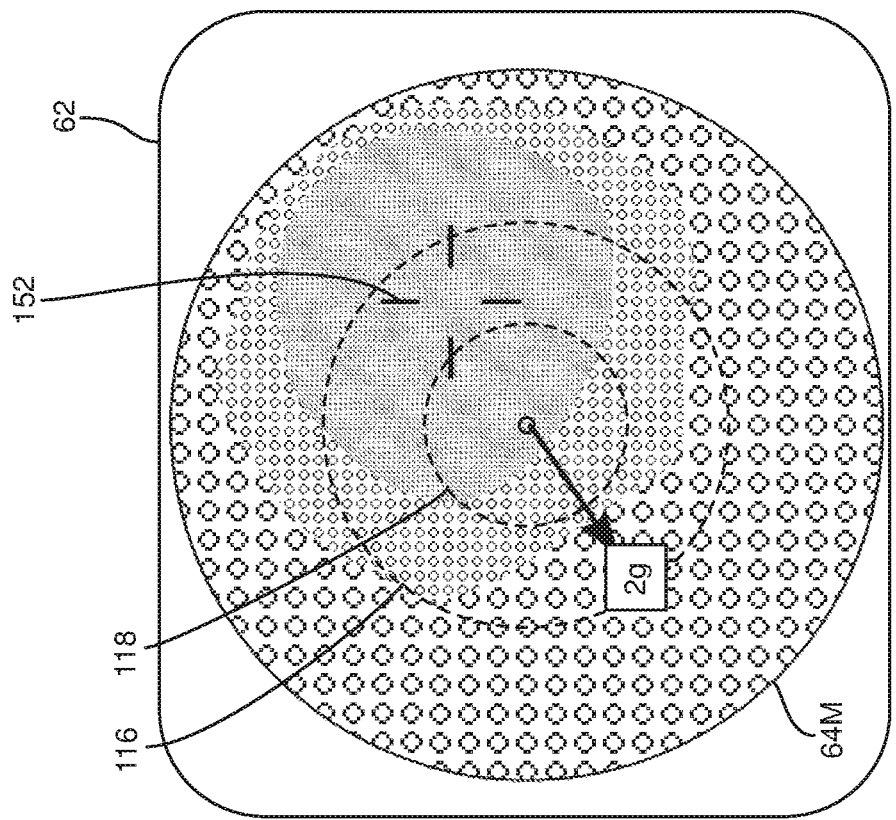
FIG. 8A and FIG. 8B are respective illustrations of single combined force-temperature maps, according to yet further disclosed embodiments of the present invention.
Figure 8A:
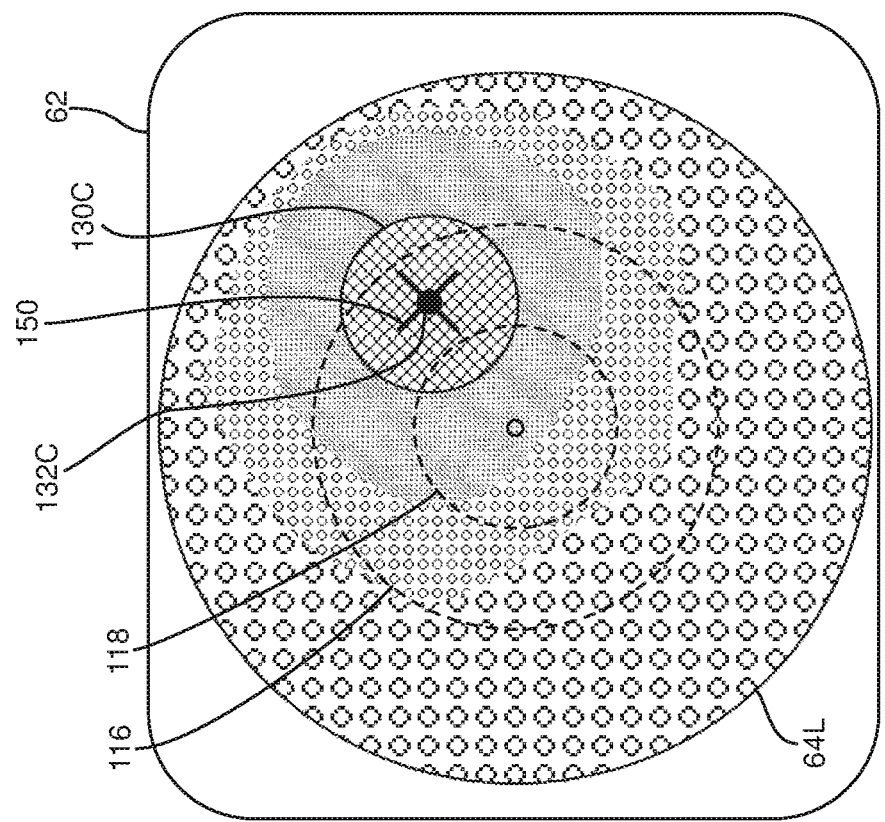

FIG. 8A and FIG. 8B are respective illustrations of a single combined force-temperature map 64L and a single combined force-temperature map 64M, according to embodiments of the present invention. The two maps have the same temperature distribution, but in map 64L the force is represented as a circle 130C with a center 132C, as described above with respect to FIG. 4A, and in map 64M the force is represented as an arrow 140C with an attached text box 142C, as described above with respect to FIG. 5A.

A center of the temperature distribution is calculated by any means known in the art. For example, the center may correspond to a weighted center of gravity of regions of the distribution, where the weights are according to the temperatures of each of the regions. In map 64L a temperature distribution center 150 is indicated by an X on the map; in map 64M a temperature distribution center 152 is indicated by cross-hairs on the map. In map 64L the force direction is shown as aligning with temperature distribution center 150, in a "bullseye" type of display, which may be the desired situation for ablation of a single region. In contrast, in map 64M the force does not align with temperature distribution center 152, and this may be the desired situation for ablation along a line.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A computer-implemented method for displaying information, comprising:
   receiving, by a computer, measurements from a probe located inside a body of a subject, the measurements being probe parameters comprising a force exerted by the probe on tissue of the subject and temperatures measured by sensors of the probe; and
   responsively to the measurements, displaying in a single map on a display screen connected to the computer a graphical representation of a distribution of the temperatures in a vicinity of the probe with a vector representation of the force superimposed on the distribution of the temperatures.

2. The computer-implemented method according to claim 1, wherein the vector representation comprises a first indication of a magnitude of the force and a second indication of a force-direction of the force.

3. The computer-implemented method according to claim 2, wherein the vector representation comprises an arrow, and wherein the first indication comprises a width of the arrow, and wherein the second indication comprises a combination of a length of the arrow and a direction of the arrow.

4. The computer-implemented method according to claim 2, wherein the vector representation comprises an arrow and a text box associated with the arrow, and wherein the first indication comprises text within the text box, and wherein the second indication comprises a combination of a length of the arrow and a direction of the arrow.

5. The computer-implemented method according to claim 2, wherein the vector representation comprises a first circle having a first center, and wherein the graphical representation of the distribution comprises a second circle having a second center, and wherein the first indication comprises a diameter of the first circle, and wherein the second indication comprises a combination of a distance between the first and second centers and a direction between the first and second centers.

6. The computer-implemented method according to claim 1, and comprising calculating a center of the graphical representation, and displaying the center in the single map.

\* \* \* \* \*